United States Patent
Inoue

(10) Patent No.: US 9,294,034 B2
(45) Date of Patent: Mar. 22, 2016

(54) MEASUREMENT DEVICE FOR TEXTURE SIZE, MANUFACTURING SYSTEM FOR SOLAR CELL, AND MANUFACTURING METHOD FOR SOLAR CELL

(71) Applicant: SANYO Electric Co., Ltd., Moriguchi-shi, Osaka (JP)

(72) Inventor: Hirotada Inoue, Hyogo (JP)

(73) Assignee: PANASONIC INTELLECTUAL PROPERTY MANAGEMENT CO., LTD (JP)

( * ) Notice: Subject to any disclaimer, the term of this patent is extended or adjusted under 35 U.S.C. 154(b) by 0 days.

(21) Appl. No.: 14/550,153

(22) Filed: Nov. 21, 2014

(65) Prior Publication Data

US 2015/0079702 A1    Mar. 19, 2015

Related U.S. Application Data

(63) Continuation of application No. PCT/JP2012/064103, filed on May 31, 2012.

(51) Int. Cl.
*H01L 31/18* (2006.01)
*H02S 50/15* (2014.01)
*G01B 11/02* (2006.01)
(Continued)

(52) U.S. Cl.
CPC ............ *H02S 50/15* (2014.12); *B05B 12/004* (2013.01); *G01B 11/02* (2013.01); *G01B 11/303* (2013.01); *G01N 21/59* (2013.01); *G01N 21/84* (2013.01); *H01L 31/02363* (2013.01); *H01L 31/022425* (2013.01); *H01L 31/0747* (2013.01); *G01N 2021/3568* (2013.01); *Y02E 10/50* (2013.01)

(58) Field of Classification Search
CPC . H01L 31/18; H01L 31/0216; H01L 31/0236; H01L 31/0224; H01L 31/02168; H01L 31/02366; H01L 29/20; H01L 29/861
USPC .......... 438/7, 71, 694; 257/618; 136/244, 295
See application file for complete search history.

(56) References Cited

U.S. PATENT DOCUMENTS 5,397,400 A    3/1995    Matsuno et al.
5,472,885 A    12/1995    Matsuno et al.
(Continued)

FOREIGN PATENT DOCUMENTS

JP    61038406 A    2/1986
JP    H0690014 A    3/1994
(Continued)

OTHER PUBLICATIONS

International Search Report for PCT/JP2012/064103; Date of Mailing: May 31, 2012, with English translation.

*Primary Examiner* — Michael Lebentritt
(74) *Attorney, Agent, or Firm* — Cantor Colburn LLP

(57) ABSTRACT

A manufacturing method for a solar cell, wherein after a texture is formed on a principal surface of a substrate, infrared light in a predetermined wave number range is applied to a portion, on which the texture is formed, of the principal surface, a wave number at a specified transmission detection rate of the infrared light transmitted through the substrate and detected is acquired, the Tx size of the substrate is calculated on the basis of the acquired wave number using a previously obtained relationship between the wave number at the specified transmission detection rate and the Tx size, and when the calculated Tx size is within a reference value range, a collecting electrode is formed on the principal surface.

17 Claims, 11 Drawing Sheets

(51) Int. Cl.
*G01N 21/84* (2006.01)
*G01N 21/59* (2006.01)
*H01L 31/0236* (2006.01)
*H01L 31/0747* (2012.01)
*B05B 12/00* (2006.01)
*G01B 11/30* (2006.01)
*H01L 31/0224* (2006.01)
*G01N 21/3563* (2014.01)

(56) References Cited

U.S. PATENT DOCUMENTS

| | | | |
|---|---|---|---|
| 5,963,790 A | 10/1999 | Matsuno et al. | |
| 2005/0162666 A1 | 7/2005 | Munzer | |
| 2010/0219506 A1* | 9/2010 | Gupta | H01L 21/02686 257/618 |
| 2011/0053310 A1* | 3/2011 | Yonezawa | H01L 31/022425 438/87 |
| 2011/0120518 A1* | 5/2011 | Rust | H01L 31/042 136/244 |
| 2013/0210187 A1 | 8/2013 | Takahama et al. | |
| 2013/0214271 A1* | 8/2013 | Asami | H01L 29/267 257/43 |
| 2013/0276860 A1* | 10/2013 | Karakida | H01L 31/068 136/244 |
| 2014/0349485 A1* | 11/2014 | Umekawa | H01L 31/02363 438/694 |
| 2015/0056743 A1* | 2/2015 | Karakida | H01L 31/02363 438/71 |
| 2015/0079702 A1* | 3/2015 | Inoue | G01B 11/02 438/7 |
| 2015/0083183 A1* | 3/2015 | Nishimoto | H01L 31/02168 136/244 |

FOREIGN PATENT DOCUMENTS

| | | |
|---|---|---|
| JP | 2001059816 A | 3/2001 |
| JP | 2003075126 A | 3/2003 |
| JP | 2006073832 A | 3/2006 |
| JP | 2007514155 A | 5/2007 |
| JP | 2011249671 A | 12/2011 |
| JP | 2012074415 A | 4/2012 |

* cited by examiner

MEASUREMENT DEVICE FOR TEXTURE SIZE, MANUFACTURING SYSTEM FOR SOLAR CELL, AND MANUFACTURING METHOD FOR SOLAR CELL

CROSS-REFERENCE TO RELATED APPLICATION

The present application is a continuation under 35 U.S.C. §120 of PCT/JP2012/064103, filed May 31, 2012, which is incorporated herein by reference.

TECHNICAL FIELD

The present invention relates to a measurement device of a texture size, a manufacturing system of a solar cell, and a manufacturing method of a solar cell.

BACKGROUND ART

In a solar cell, in order to reduce surface reflection of light and improve light reception efficiency, a texture which is a very fine unevenness (projections and depressions) structure is formed on a primary surface of a substrate (for example, Patent Document 1).

RELATED ART REFERENCE

Patent Document

[Patent Document 1] JP 2012-074415 A

DISCLOSURE OF INVENTION

Technical Problem

For example, when a texture size is to be managed in the manufacturing process of a solar cell, a quick method of measurement is desired.

Solution to Problem

According to one aspect of the present invention, there is provided a measurement device of a texture size, comprising: a light source that emits an infrared ray in a predetermined wave number range; a holder that holds a substrate for a solar cell over which a texture is formed such that the infrared ray is incident over a primary surface of the substrate; and a detector that detects an intensity of the infrared ray transmitted through the substrate.

According to another aspect of the present invention, there is provided a manufacturing system of a solar cell, comprising: the measurement device; a unit that forms the texture over the primary surface of the substrate; and a unit that forms a collecting electrode over the primary surface. According to another aspect of the present invention, preferably, the holder of the measurement device is of a movable type which can hold a plurality of substrates and which can transport the substrates in the horizontal direction.

According to another aspect of the present invention, there is provided a method of manufacturing a solar cell, comprising: after forming a texture over a primary surface of a semiconductor substrate, irradiating an infrared ray in a predetermined wave number range on apart of the primary surface over which the texture is formed; acquiring a wave number at a particular transmission detection ratio of the infrared ray transmitted through the substrate and detected, or at a particular reflection detection ratio of the infrared ray reflected by the substrate and detected; and forming a collecting electrode over the primary surface when the wave number is greater than or equal to a threshold wave number. According to another aspect of the present invention, preferably, a size of the texture of the substrate is calculated based on the acquired wave number using a predetermined relationship between the wave number at the particular transmission detection ratio or at the particular reflection detection ratio and the texture size, and the collecting electrode is formed over the primary surface when the calculated texture size is less than or equal to a threshold size.

Advantageous Effects of Invention

According to various aspects of the present invention, the texture size can be quickly measured.

BEST MODE FOR CARRYING OUT THE INVENTION

A preferred embodiment of the present invention will now be described in detail with reference to the drawings. The present invention is not limited to the preferred embodiment described below. In addition, the drawings referred to in the preferred embodiment are schematically shown, and the sizes and ratios of the constituent elements drawn in the figures should be determined in consideration of the description below.

In the present specification, the term "wave number" is primarily used. However, as "wave number" is an inverse of a "wavelength", that is, the wave number is 1/wavelength, the description of the present specification may also be read in terms of "wavelength" in place of "wave number" while converting "wave number" to "wavelength".

Figure 1:
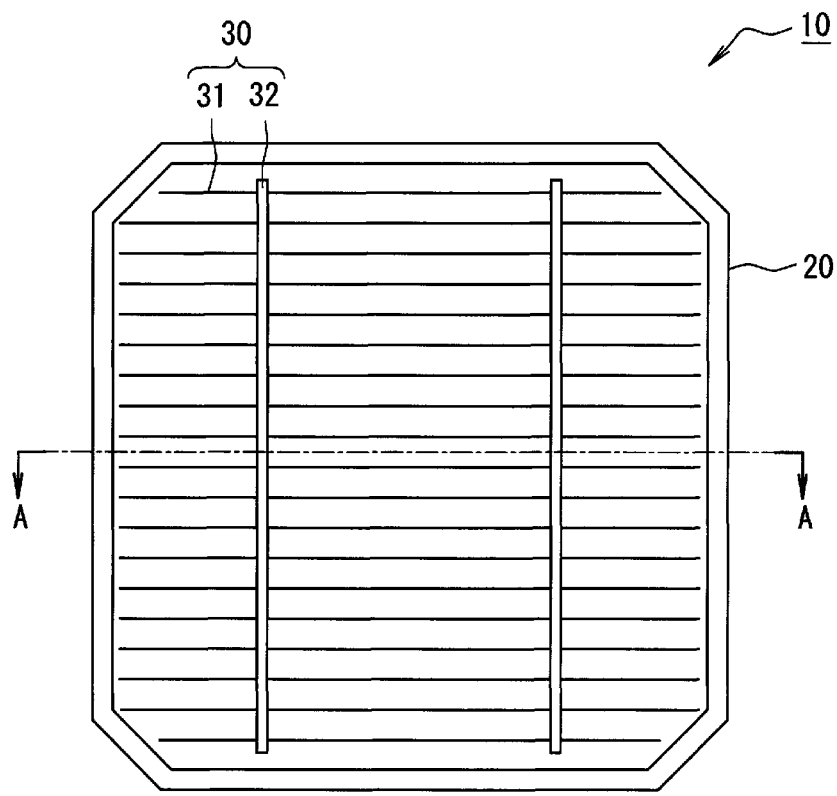
FIG. 1 is a plan view showing an example solar cell according to a preferred embodiment of the present invention, viewed from a side of a light receiving surface.
Figure 2:
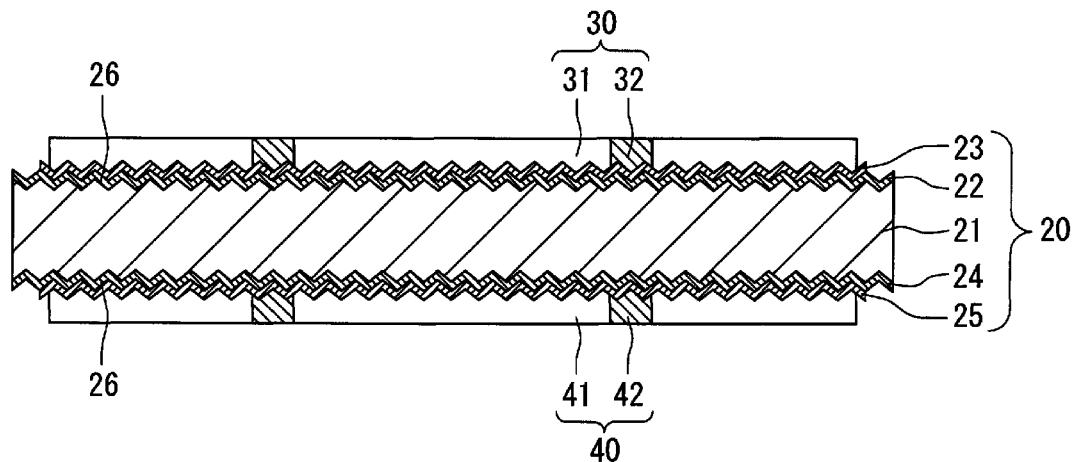
FIG. 2 is a cross sectional diagram along an A-A line in FIG. 1.

A structure of a solar cell 10 obtained by a manufacturing method described later will now be briefly described with reference to FIGS. 1 and 2. FIG. 1 is a plan view of the solar cell 10 viewed from a side of a light receiving surface. FIG. 2 is a cross sectional diagram cutting the solar cell 10 in the thickness direction along an A-A line of FIG. 1.

The solar cell 10 includes a photoelectric conversion unit 20 that receives light such as solar light and produces carriers, a first electrode 30 which is a light receiving surface electrode provided over the light receiving surface of the photoelectric conversion unit 20, and a second electrode 40 which is a back surface electrode provided over a back surface of the photoelectric conversion unit 20. On the back surface of the solar cell 10, because the effect of light shielding loss for the photoelectric conversion characteristic is smaller compared to the light receiving surface, normally, the second electrode 40 is formed with a larger area than the first electrode 30.

A "light receiving surface" refers to a primary surface through which the solar light primarily enters from the outside of the solar cell 10. For example, of the solar light entering the solar cell 10, 50%~100% of the solar light enters from the side of the light receiving surface. A "back surface" refers to a primary surface on a side opposite of the light receiving surface. In other words, of the primary surfaces, the surface having a larger electrode area is the back surface.

The photoelectric conversion unit 20 has a substrate 21 made of a semiconductor material such as, for example, crystalline silicon (c-Si), gallium arsenide (GaAs), indium phosphide (InP), or the like. As the substrate 21, an n-type monocrystalline silicon substrate is preferable, and an n-type monocrystalline silicon substrate having a (100)-plane as the primary surface is particularly preferable.

Over the light receiving surface of the substrate 21, an amorphous semiconductor layer 22, and a transparent conductive layer 23 made of a light-transmissive conductive oxide (TCO) having indium oxide or the like as a primary composition are sequentially formed. Over the back surface of the substrate 21, an amorphous semiconductor layer 24, and a transparent conductive layer 25 are sequentially formed. The amorphous semiconductor layer 22 has, for example, a multilayer structure in which an i-type amorphous silicon layer and a p-type amorphous silicon layer are sequentially formed. The amorphous semiconductor layer 24 has, for example, a multilayer structure in which an i-type amorphous silicon layer and an n-type amorphous silicon layer are sequentially formed.

A texture 26 which is a very fine unevenness structure is formed over the substrate 21, in order to reduce reflection of light and improve light reception efficiency. The texture 26 is preferably formed over approximately the entire region over the light receiving surface and the back surface of the substrate 21. Here, "approximate entire region" refers to a range which can substantially be assumed to be the entire region, and is, for example, a region of greater than or equal to 95% of the light receiving surface. The texture 26 has, for example, approximately the same size over the approximately entire region of the primary surface and over the light receiving surface and the back surface. In the present specification, the size of the texture 26 (hereinafter also referred to as a "Tx size") refers to a size in a state where the primary surface of the substrate 21 is viewed in the plan view, that is, in a state viewed from a vertical direction with respect to the primary surface. The definition of the Tx size is not particularly limited, and in the following, the Tx size means a diameter of a circumscribing circle of the texture 26. The Tx size also means an average within a range of greater than or equal to 1 mm² of the primary surface.

A specific example of the texture 26 is an unevenness structure of a pyramid shape (a rectangular cone or a rectangular frustum shape) obtained by applying anisotropic etching on an n-type monocrystalline silicon substrate having the (100)-plane as the primary surface. The Tx size is preferably about 0.5 μm~20 μm. A depth of a depression of the texture 26 is, for example, about a few μm. Thicknesses of the amorphous semiconductor layers 22 and 24 are, for example, a few nm-a few tens of nm, and thicknesses of the transparent conductive layers 23 and 25 are, for example, about a few tens of nm to a few hundreds of nm. Therefore, the texture 26 appears also over these thin film layers.

The first electrode 30 is formed by a plurality of (for example, 50) finger portions 31, and a plurality of (for example, 2) bus bar portions 32. The finger portion 31 is a collecting electrode of a narrow line shape formed over a wide range of the light receiving surface in order to collect carriers produced by the photoelectric conversion unit 20. The bus bar portion 32 is a collective electrode that collects the carriers from the finger portion 31, and is electrically connected to all of the finger portions 31 (hereinafter the finger portion and the bus bar portion may collectively be referred to as a "collecting electrode"). In the first electrode 30, two bus bar portions 32 are placed in parallel to each other with a predetermined gap therebetween, and the plurality of finger portions 31 are placed to intersect the bus bar portions. The plurality of finger portions 31 are placed such that apart thereof extends from each of the bus bar portions 32 toward an end edge side of the light receiving surface, and the remaining part connects the two bus bar portions 32.

Similarly, the second electrode 40 is formed by a plurality of (for example, 250) finger portions 41 and a plurality of (for example, 2) bus bar portions 42, and has an electrode placement similar to that of the first electrode 30. When light reception from the side of the back surface is not expected, a metal layer such as silver may be provided in place of the finger portion 41. In this case also, the texture 26 is preferably formed over the back surface of the substrate 21.

A manufacturing system 50 of a solar cell (hereinafter referred to as "manufacturing system 50") having a measurement device 60 of a texture size (hereinafter referred to as a "measurement device 60") and a manufacturing method of the solar cell 10 will now be described with reference to FIGS. 3-14. In the following, the substrate 21 before the texture 26 is formed will be referred to as a "substrate 21*b*".

Figure 3:
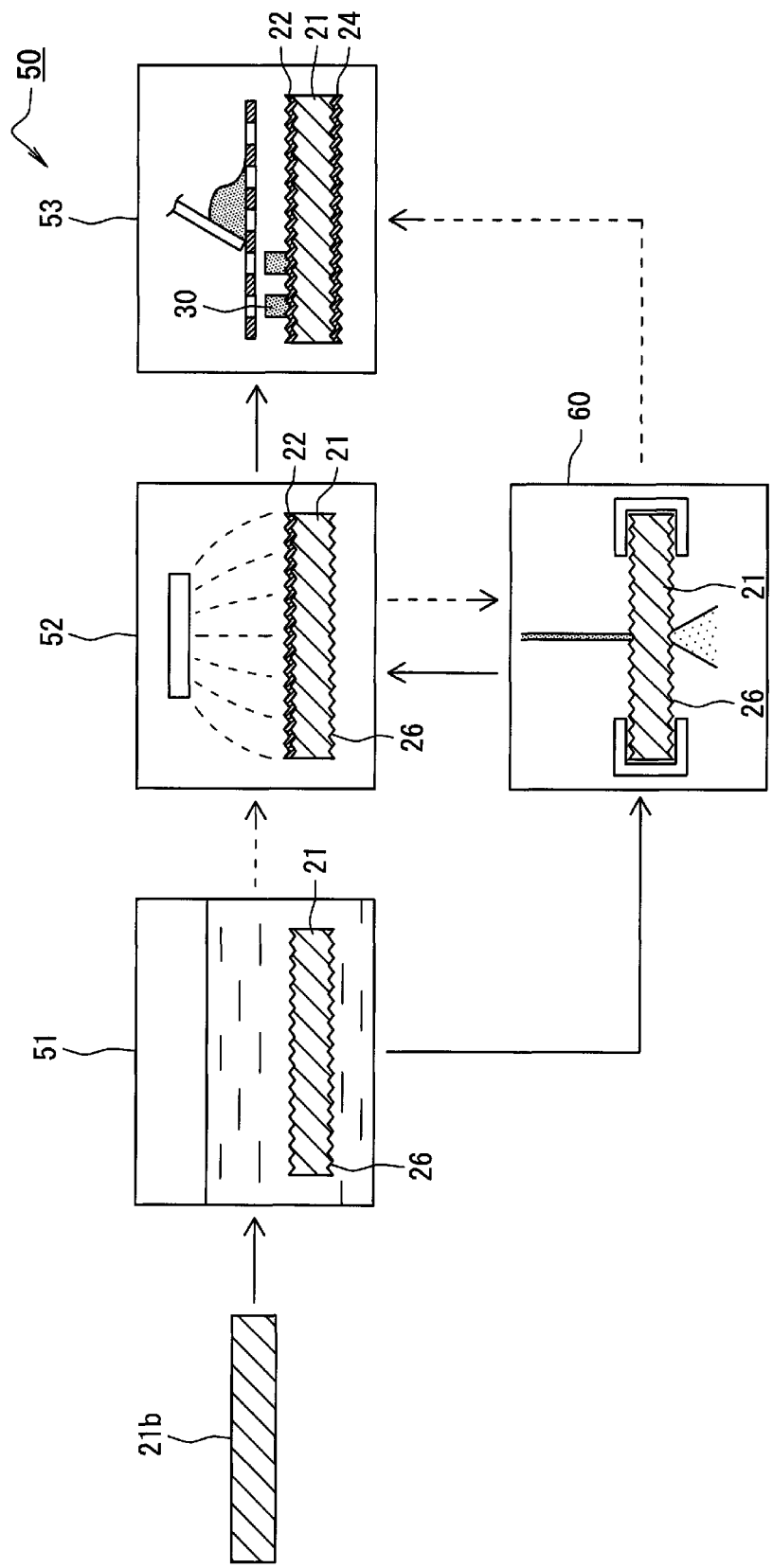
FIG. 3 is a block diagram showing an example manufacturing system of a solar cell according to a preferred embodiment of the present invention.

FIG. 3 is a block diagram showing the manufacturing system 50. In FIG. 3, steps exemplified in FIGS. 11 and 12 to be described later are shown with solid line arrows and steps exemplified in FIGS. 13 and 14 to be described later are shown with broken line arrows. The manufacturing system 50 includes a texture formation unit 51, a thin film layer formation unit 52, an electrode formation unit 53, and the measurement device 60. The manufacturing system 50 may automatically execute all steps or, alternatively, a manual operation may be applied to a part of the steps, for example, a part of the transportation of the substrate 21 or the like or the process in each unit.

In the texture formation unit 51, the texture 26 is formed over the primary surface of the substrate 21b. The texture formation unit 51 has, for example, a treatment tank filled with an etchant. The substrate 21b is immersed in the etchant, so that the texture 26 is formed over the light receiving surface and the back surface. As a preferable etchant, for example, when the substrate 21b is a monocrystalline silicon substrate having the (100)-plane, an alkali etchant such as a sodium hydroxide (NaOH) etchant and a potassium hydroxide etchant (KOH) may be exemplified. By changing the substrate 21 to be used, a concentration of the etchant, a treatment period, or the like, it is possible to adjust the Tx size. Alternatively, the texture 26 may be formed using an etching gas.

In the thin film layer formation unit 52, the amorphous semiconductor layers 22 and 24 are formed over the primary surface of the substrate 21 over which the texture 26 is formed. Preferably, the transparent conductive layers 23 and 25 are formed over the amorphous semiconductor layers 22 and 24, respectively. The thin film layer formation unit 52 has, for example, a CVD device or a sputtering device. For the formation of the i-type amorphous semiconductor layer by CVD, for example, material gas in which silane gas ($SiH_4$) is diluted by hydrogen ($H_2$) is used. In the case of the n-type amorphous semiconductor layer, for example, a material gas in which phosphine ($PH_3$) is added to silane ($SiH_4$), and the mixture gas is diluted by hydrogen ($H_2$) is used. In the case of the p-type amorphous semiconductor layer, for example, diborane ($B_2H_6$) is used as the doping gas in place of the phosphine ($PH_3$).

In the electrode formation unit 53, the collecting electrode is formed over the substrate 21 over which layers such as the amorphous semiconductor layers 22 and 24, and the like are formed. The electrode formation unit 53 has, for example, various printing devices and electroplating device. The printing method for forming the collecting electrode is not particularly limited so long as the method can print a conductive paste over the primary surface, but from the viewpoint of the productivity or the like, stencil printing such as an offset printing and a screen printing is preferable. FIG. 3 shows a screen printing device which prints the conductive paste using a screen plate and a squeegee.

The measurement device 60 measures a size of the texture 26 formed by the texture formation unit 51. In the manufacturing system 50, the substrate 21 is supplied to the measurement device 60 after the texture 26 is formed and before the collecting electrode is formed, and the Tx size is measured. Preferably, only a substrate 21 having the Tx size within a target range as a result of the measurement of the Tx size is supplied to the electrode formation unit 53.

Figure 4:
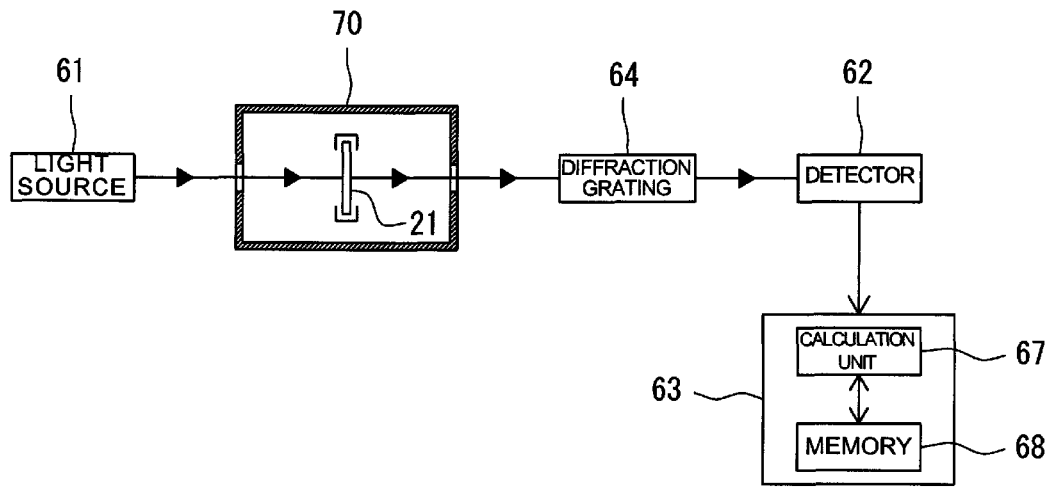
FIG. 4 is a block diagram showing a first example measurement device of a texture size according to a preferred embodiment of the present invention.
Figure 5:
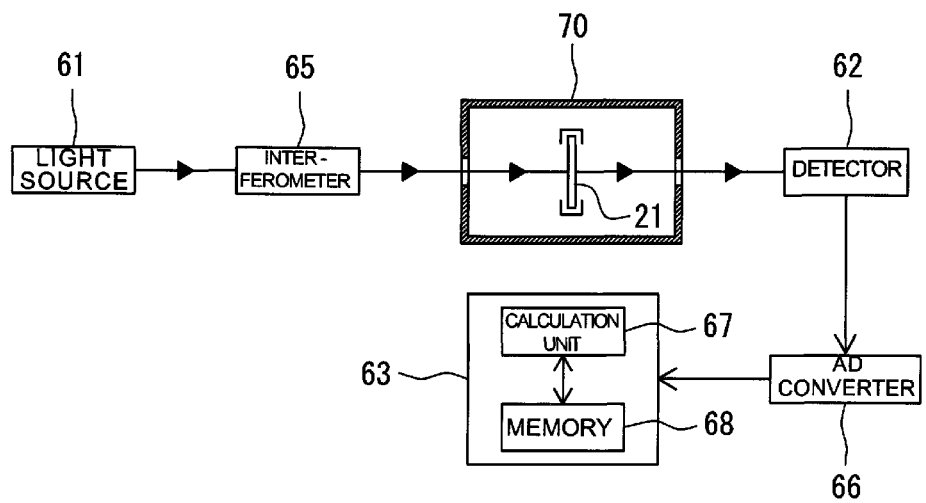
FIG. 5 is a block diagram showing a second example measurement device of a texture size according to a preferred embodiment of the present invention.

FIGS. 4 and 5 are block diagrams of the measurement device 60. The measurement device 60 is a device that irradiates an infrared ray toward the primary surface of the substrate 21 which is a substrate for a solar cell over which the texture 26 is formed, and detects the infrared ray transmitted through the substrate 21, to measure the Tx size. A structure of a known infrared spectrophotometer may be applied as apart of the measurement device 60. In an example structure shown in FIG. 4, a dispersion infrared spectrophotometer (hereinafter referred to as a "dispersion IR") is applied. In an example structure shown in FIG. 5, a Fourier transform infrared spectrophotometer (hereinafter referred to as an "FT-IR") is applied.

The measurement device 60 includes a light source 61 that emits an infrared ray within a predetermined wave number range, and a detector 62 that detects intensity of the infrared ray transmitted through the substrate 21. Here, the "intensity" is used in the same meaning as "amount of light". A sample chamber 70 in which the substrate 21 is set is provided between the light source 61 and the detector 62. The infrared ray emitted from the light source 61 enters the sample chamber 70, is irradiated on the substrate 21, and transmits through the substrate 21, and the transmitted infrared ray is detected by the detector 62. The measurement device 60 further includes a computer 63 that processes detection information by the detector 62. In the present embodiment, the measurement device 60 includes the sample chamber 70, but alternatively, the measurement device 60 may have a structure which does not have a chamber such as a sample chamber 70 and only has a holder 73 to be described later or only has the holder 73 and a light blocking plate 74 to be described later.

For the light source 61, preferably, a lamp that can emit an infrared ray of a wavelength of about 2 times~10 times the Tx size to be measured is preferably used. As the predetermined wave number range described above, a range of about 50 $cm^{-1}$~10000 $cm^{-1}$ is preferable, but the range is preferably suitably changed according to the size to be measured or the like, from the viewpoint of reduction of the cost of the device. The predetermined wave number range may be, for example, about 500 $cm^{-1}$~10000 $cm^{-1}$, or about 1000 $cm^{-1}$~5000 $cm^{-1}$. A size of an irradiation spot of the infrared ray is not particularly limited, but is set, from the viewpoint of the measurement precision or the like, to a size which at least includes many textures 26 in the spot, for example, about 1 $mm^2$~5 $mm^2$. The detector 62 can be suitably selected according to the light source 61 or the like. For example, a DTGS detector or an MTC detector may be used. For an optical system, a structure of a known infrared spectrophotometer may be applied. For example, either of a single-beam type device or a double-beam type device may be employed.

In the case of the dispersion IR shown in FIG. 4, a diffraction grating 64 is provided between the sample chamber 70 and the detector 62. The diffraction grating 64 has a function to separate the infrared ray transmitted through the substrate 21 and emitted from the sample chamber 70. Normally, a slit (not shown) is provided between the diffraction grating 64 and the detector 62. An orientation of the diffraction grating 64 is scanned, to continuously change the wavelength of the infrared ray passing through the slit, and the infrared ray passing through the slit is detected by the detector 62. The computer 63 produces, for example, a spectrum showing the intensity at each wave number of the detected infrared ray.

In the case of the FT-IR shown in FIG. 5, in place of the diffraction grating 64, an interferometer 65 and an AD converter 66 are provided. For example, the interferometer 65 is provided between the light source 61 and the sample chamber 70, and the AD converter 66 is provided between the detector 62 and the computer 63. In the FT-IR, interference light obtained by the interferometer is converted into a digital signal by the AD converter 66, and then the digital signal is Fourier transformed, to separate the light. In this case, the computer 63 has, for example, a function to Fourier-transform the digital signal, in addition to the above-described function to produce the spectrum.

The computer 63 further includes a calculation unit 67 that calculates the Tx size based on the detection information by the detector 62, for example, the detection information to which the above-described process is applied, and a memory 68 that stores information necessary for calculating the Tx size. A certain relationship exists between the transmitted light (hereinafter also referred to as "transmitted and detected light") transmitted through the substrate 21 and detected by the detector 62, among the infrared ray irradiated onto the substrate 21, and the Tx size, as will be described below. The measurement device 60 can measure the Tx size using this relationship. With the use of the transmitted light, Tx sizes of both the texture 26 on the light receiving surface side and the texture 26 on the back surface side can be simultaneously measured. In other words, because the transmitted and detected light is light transmitted through both primary surfaces, the light includes information of Tx sizes of both primary surfaces. However, when the texture 26 exists both over the light receiving surface and over the back surface, it is difficult to measure only the Tx size of one surface using the transmitted light.

Figure 6:
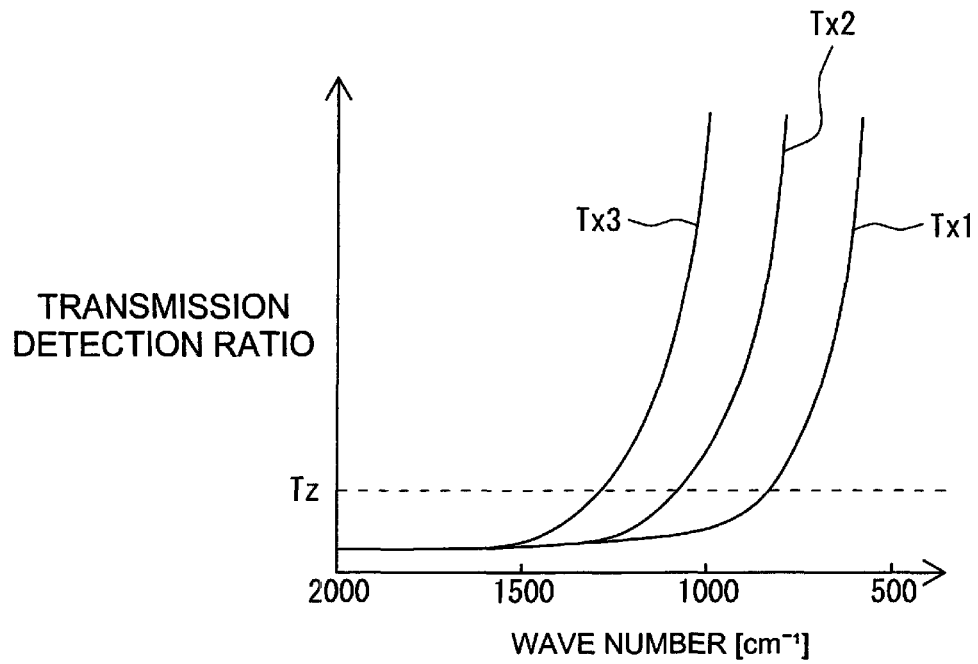
FIG. 6 is a diagram showing a relationship between a transmission and detection ratio of an infrared ray and a wave number in a preferred embodiment of the present invention.

FIG. 6 shows a relationship between a transmission and detection ratio of an infrared ray and the wave number in the textures 26 having different Tx sizes from each other (with the Tx size being Tx1>Tx2>Tx3). The transmission and detection ratio refers to a ratio of the infrared ray transmitted through the substrate 21 and that detected by the detector 62 over the infrared ray entering the substrate 21, and normally, is determined by (intensity of infrared ray emitted from the sample chamber 70)*100/(intensity of infrared ray entering the sample chamber 70).

As shown in FIG. 6, in any of the Tx sizes, when the wave number of an infrared ray exceeds a predetermined value, the transmission and detection ratio shows a constant value. When the wave number of the infrared ray exceeds a predetermined value, the transmission and detection ratio is, for example, 0 or a value near 0. On the other hand, when the wave number of the infrared ray is less than or equal to the predetermined value, the transmission and detection ratio increases rapidly. When the wave number of the infrared ray is less than or equal to the predetermined value, for example, the transmission and detection ratio increases exponentially with respect to the wave number. In other words, the predetermined value may be considered to be a threshold where the infrared ray (transmitted light) transmitted through the substrate 21 starts to enter the detector 62 and to be detected, or a threshold where the component entering the detector 62 is increased and the detection intensity starts to increase (hereinafter the predetermined value will be referred to as a "detection threshold"). The detection threshold differs according to the Tx size. The measurement device 60 can quickly measure the Tx size using this relationship.

Specifically, as the Tx size is reduced, the detection threshold is increased. In other words, as the Tx size becomes smaller, the detection threshold for the wavelength becomes smaller. This is because the extent of scattering of the infrared ray differs depending on the Tx size, and the scattering of the infrared ray by the texture 26 tends to more easily occur as the TX size becomes smaller. For example, when the wave number of the infrared ray irradiated on the texture 26 having the Tx size of Tx1 is smaller than the detection threshold (for example, when the wavelength of the infrared ray is twice the Tx size), the infrared ray is scattered and diffused by the texture 26, and the amount of a component entering the detector 62 is low. On the other hand, when the wave number of the infrared ray is greater than the detection threshold (in a case where the wavelength of the infrared ray is sufficiently longer than the Tx size; for example, when the wavelength is 10 times the Tx size), the amount of a component scattered by the texture 26 is small, and the amount of a component entering the detector 62 is increased.

The infrared ray is not scattered by the texture when the wave number thereof is greater than the detection threshold, and the infrared ray is scattered when the wave number thereof is smaller than the detection threshold. The detection threshold is primarily determined by the Tx size, and is not significantly affected by the texture shape. Even when a defect such as a structure with a different angle is included in the textures which exist in a large number, the detection threshold is primarily determined by the Tx size. Because of this, in the present method, the Tx size can be measured with a high precision without being affected by the defect of the texture or the like.

Figure 7:
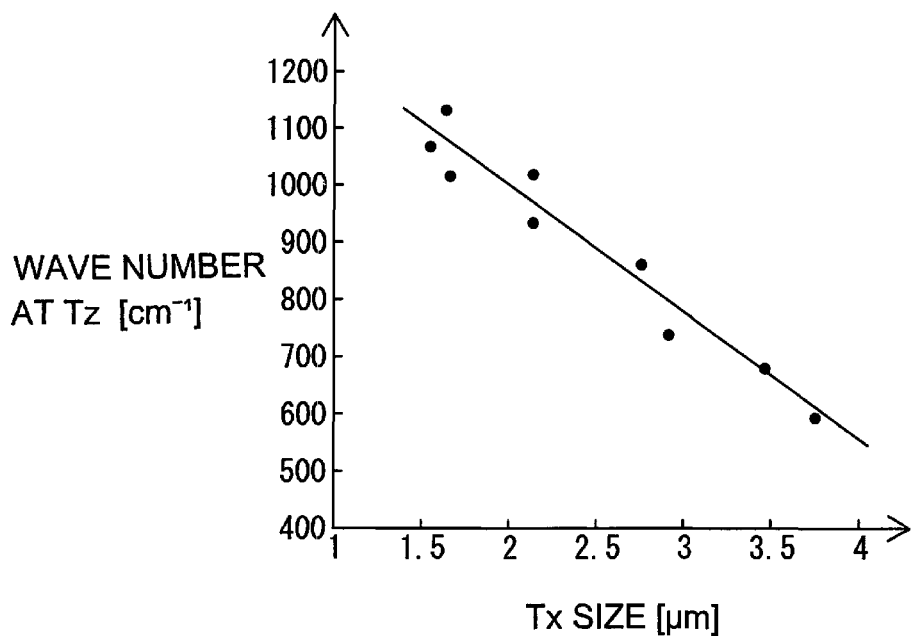
FIG. 7 is a diagram showing a relationship between a wave number at a particular transmission and detection ratio of an infrared ray detected for a standard substrate and a texture size of the standard substrate in a preferred embodiment of the present invention.

FIG. 7 shows a relationship between a wave number of a particular transmission and detection ratio Tz of the infrared ray detected for a standard substrate and the Tx size of the standard substrate. Here, a "standard substrate" refers to a substrate having a known Tx size, and is used for determining the Tx size of the substrate 21. The standard substrate has the same structure as the substrate 21. The Tx size of the standard substrate is measured by a known method, for example, using an SEM. The particular transmission detection ratio Tz is set from a range where the transmission detection ratio does not become the constant value for the Tx size to be measured, that is, from a range where the transmission and detection ratio is exponentially increased with respect to the wave number (refer to FIG. 6).

As shown in FIG. 7, there is a fair correlation between the wave number at the particular transmission detection ratio Tz and the Tx size measured by the SEM. In other words, the Tx size of the substrate 21 can be determined with a high precision based on the wave number at the particular transmission detection ratio Tz. The measurement device 60 preferably stores the relationship shown in FIG. 7 in the form of a calculation formula or a lookup table in the memory 68. The calculation unit 67 acquires, for example, the wave number at the particular transmission detection ratio Tz based on the detection information or the processed detection information, and applies the wave number to the calculation formula, lookup table, or the like stored in the memory 68, to calculate the Tx size of the substrate 21.

Figure 8:
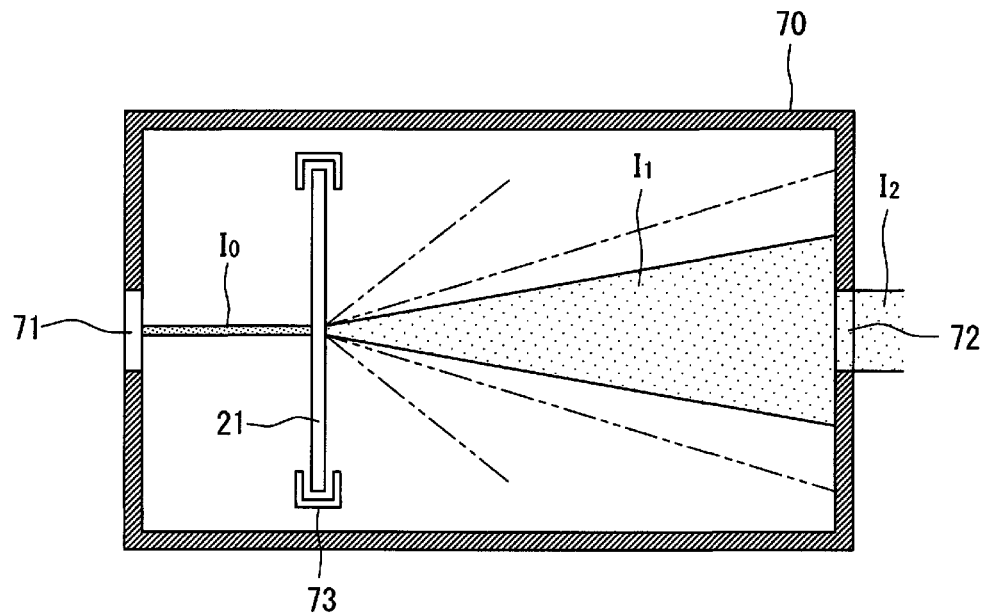
FIG. 8 is a diagram showing a first example sample chamber in a preferred embodiment of the present invention.
Figure 9:
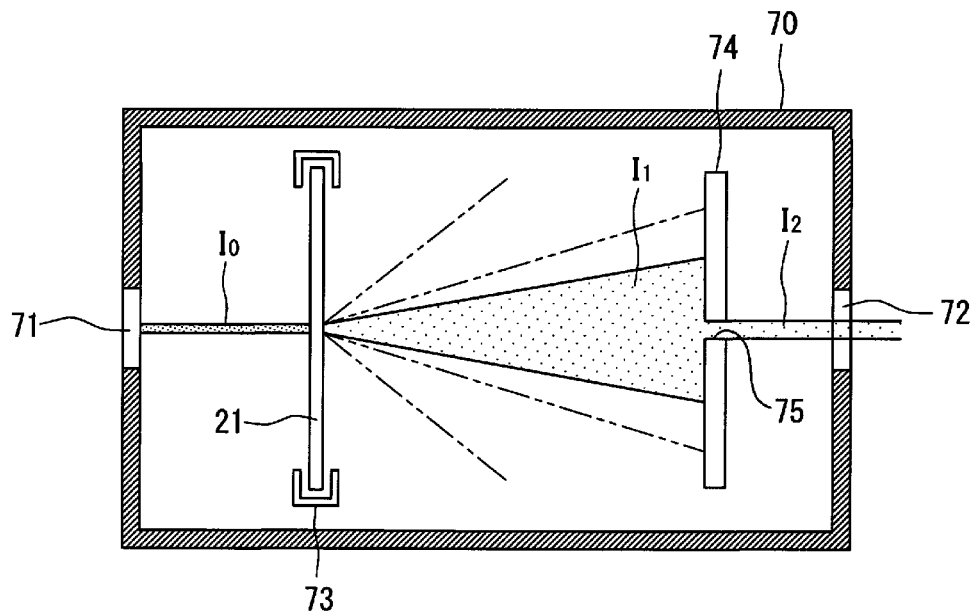
FIG. 9 is a diagram showing a second example sample chamber in a preferred embodiment of the present invention.

FIGS. 8 and 9 show an example of the sample chamber 70. In the sample chamber 70 exemplified in FIGS. 8 and 9, the substrate 21 is set one at a time. Because of this, the structure of the sample chamber 70 is preferable, for example, in a spot inspection of the substrate 21 in the manufacturing process of the solar cell 10 or in a condition determination for the formation step of the texture 26.

In the sample chamber 70, an incident window 71 which is an entrance of the infrared ray emitted from the light source 61, a detection window 72 which is an exit of the infrared ray, and a holder 73 which holds the substrate 21 so that the infrared ray is incident on the primary surface of the substrate 21, are provided. The sample chamber 70 is, for example, a chamber having a rectangular shape viewed from the above. The incident window 71 and the detection window 72 are provided on wall surfaces of the sample chamber 70 which oppose each other. The windows are preferably placed so that in a state where the substrate 21 is not set, all of the infrared ray entering from the incident window 71 exits from the detection window 72.

The holder 73 preferably holds the substrate 21 so that the infrared ray entering from the incident window 71 enters approximately perpendicularly onto the primary surface of the substrate 21. Here, the "approximate perpendicular" refers to a range that can be substantially assumed to be perpendicular, and is, for example, a range of angle between the primary surface and the infrared ray of 90°±5°. With such a configuration, the angle of incidence of the infrared ray on the substrate 21 can be stabilized and the measurement precision can be improved. The holder 73 holds, for example, the substrate 21 in a standing state, that is, a state where the primary surface is along the vertical direction. In the holder 73, a base where the substrate 21 can be placed and a pillar-shaped support section provided in a vertical arrangement along the vertical direction on the base are provided. For example, two support sections are provided, and each support section has a recess or a channel into which the substrate 21 can be inserted and supported between the support sections. According to such a structure, the ends of the substrate 21 along the vertical direction can be stably supported from both sides of the light receiving surface and the back surface without blocking transmission of the infrared ray. Alternatively, a contact area between the holder 73 and the substrate 21 may be set small, to inhibit contamination of the substrate 21.

In the holder 73, preferably, at least a part contacting the substrate 21 is made of a resin. Alternatively, the entirety of the holder 73 may be made of a resin. With such a configuration, contamination of the substrate 21 by metal ions or the like can be inhibited. The resin forming the holder 73 is not particularly limited, and for example, an acrylic resin, an olefin resin, a vinyl chloride resin, or the like may be exemplified.

The holder 73 is preferably of a movable type so that the holder 73 moves, to allow setting of a plurality of irradiation spots of the infrared ray on the primary surface while a vertical distance from the light source 61 and the detector 62 to the primary surface is maintained. With such a configuration, the Tx size can be measured at a plurality of locations easily and quickly, and consequently, the measurement precision can be improved or an in-plane distribution of the Tx size can be measured. The holder 73 is placed, for example, on a uniaxial stage to which a stepping motor is attached. In this case, the uniaxial direction in which the holder 73 moves is, for example, a direction orthogonal to a direction connecting the incident window 71 and the detection window 72 and the vertical direction. Alternatively, the holder 73 may be placed on a biaxial stage, to allow sliding of the holder 73 in the vertical direction in addition to the above-described uniaxial direction. Alternatively, the stage may be of a manually operated type.

Referring now to FIGS. 8 and 9, the relationship between the transmitted and detected light and the Tx size will now be further described. When the infrared ray entering the sample chamber 70 and irradiated onto the substrate 21 (hereinafter referred to as "incident light $I_0$") has a wavelength sufficiently longer than the Tx size, a part of the incident light $I_0$ becomes transmitted light $I_1$ transmitted through the substrate 21, and another part is absorbed by the substrate 21 or scattered by the texture 26, and does not transmit through the substrate 21. A part of the transmitted light $I_1$ becomes transmitted and detected light $I_2$ exiting from the detection window 72 and incident on the detector 62, but because the transmitted light $I_1$ also includes a scattered component caused by the texture 26, a part thereof reaches the wall surface of the sample chamber 70 and does not exit from the detection window 72. When, on the other hand, the wavelength of the incident light $I_0$ is not sufficiently longer than the Tx size, the incident light $I_0$ tends to be easily scattered by the texture 26, and the amount of light of the transmitted light $I_1$ is lower than that when the wavelength is long. In addition, the scattered component included in the transmitted light $I_1$ is increased, and the transmitted light $I_1$ is diffused in a manner as shown by a two-dots-and-chain line. In other words, as the Tx size is reduced, the amount of light of the transmitted and detected light $I_2$ is reduced. Because the intensity of the transmitted light $I_1$ itself also differs depending on the Tx size, it is also possible to detect all of the transmitted light $I_1$ by the detector 62 and measure the Tx size.

In addition, in the sample chamber 70 exemplified in FIG. 9, a light blocking plate 74 is provided which blocks the scattered light, among the infrared ray transmitted through the substrate 21, scattered by the substrate 21, that is, the scattered component included in the transmitted light $I_1$. The light blocking plate 74 is provided between the holder 73 and the detection window 72. In the light blocking plate 74, a slit 75 through which transmitted light having a small amount of scattered component can pass is formed. The slit 75 is formed, for example, on a virtual line connecting the incident window 71 and the detection window 72. With such a configuration, for example, incidence of light due to diffused reflection of the scattered component into the detector 62 can be inhibited, and the measurement precision can be improved.

Figure 10:
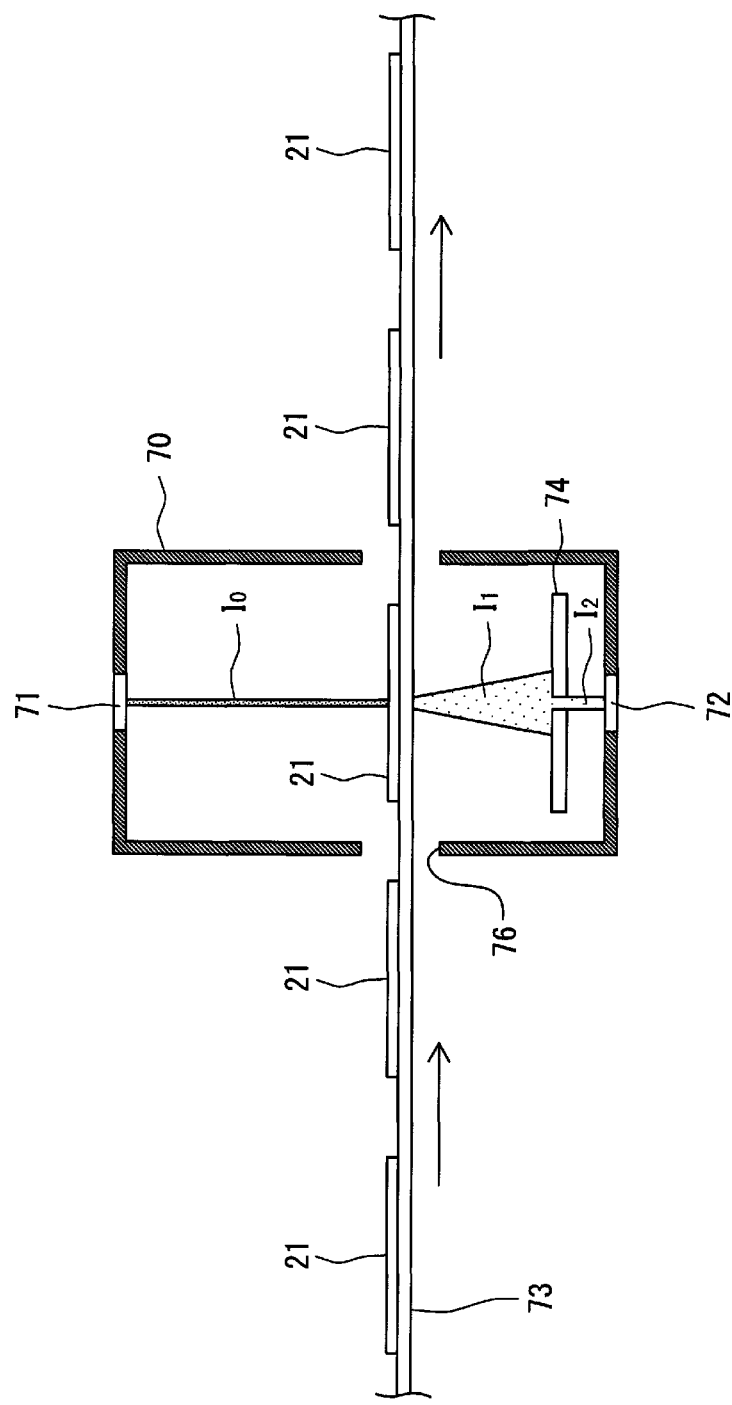
FIG. 10 is a diagram showing a third example sample chamber in a preferred embodiment of the present invention.

FIG. 10 shows another example structure of the sample chamber 70. The substrate 21 can be successively supplied to the sample chamber 70 exemplified in FIG. 10. Because of this, the exemplified structure of the sample chamber 70 is preferable, for example, for a complete inspection of the substrates 21 in the manufacturing process of the solar cell 10.

In the sample chamber 70 exemplified in FIG. 10, the holder 73 which holds the substrate 21 so that the primary surface is along the horizontal direction is provided. The holder 73 has a shape extending longer in one direction, and can hold a plurality of substrates 21 in a line in the one direction. The line of the holder 73 is not limited to one line, and a plurality of lines may be provided. The light source 61 and the incident window 71 are preferably provided above the holder 73 in the vertical direction, and the detector 62 and the detection window 72 are preferably placed below the holder 73 in the vertical direction. In this case, the infrared ray entering from the incident window 71 propagates along the vertical direction, and is approximately vertically irradiated on the substrate 21.

The holder 73 is preferably of a movable type that allows transportation of the substrates 21 in the horizontal direction along which the plurality of substrates 21 are lined, and may be, for example, of a conveyer form. Alternatively, a structure may be employed in which a plurality of holders 73 are placed in a line on a conveyer. In the sample chamber 70, an opening 76 through which the conveyer can enter and exit the chamber is formed. The conveyer is not particularly limited, but a structure that does not block the transmitted light $I_1$ is required. For example, a belt conveyer or a plate conveyer on which a hole through which the transmitted light $I_1$ is transmitted is formed may be employed. The size of the hole is preferably designed to reduce the contact area between the substrate 21 and the conveyer within a range that does not affect the holding capability of the substrate 21, from the viewpoint of inhibition of contamination of the substrate 21 or the like. In addition, it is preferable that at least a part of the conveyer contacting the substrate 21 is made of a resin.

Figure 11:
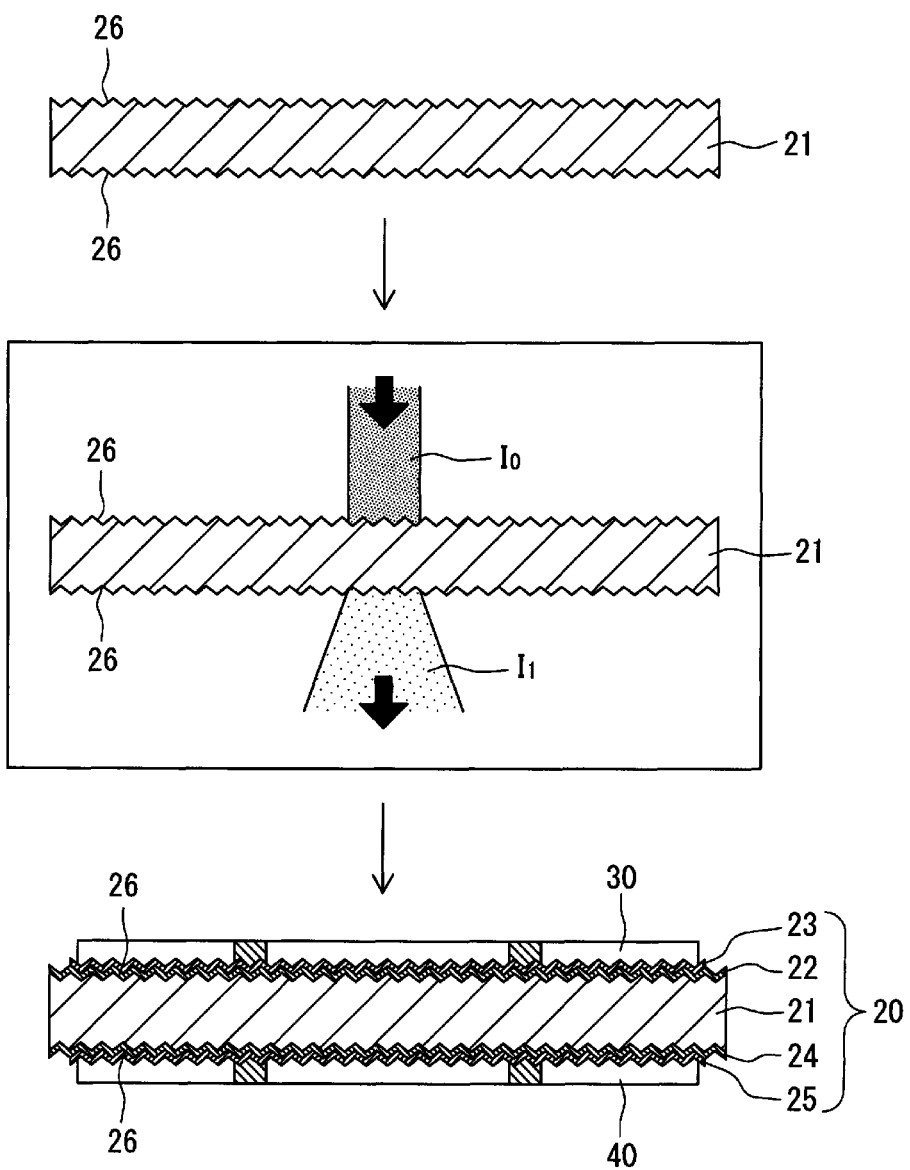
FIG. 11 is a diagram for explaining a first example manufacturing method of a solar cell according to a preferred embodiment of the present invention.
Figure 12:
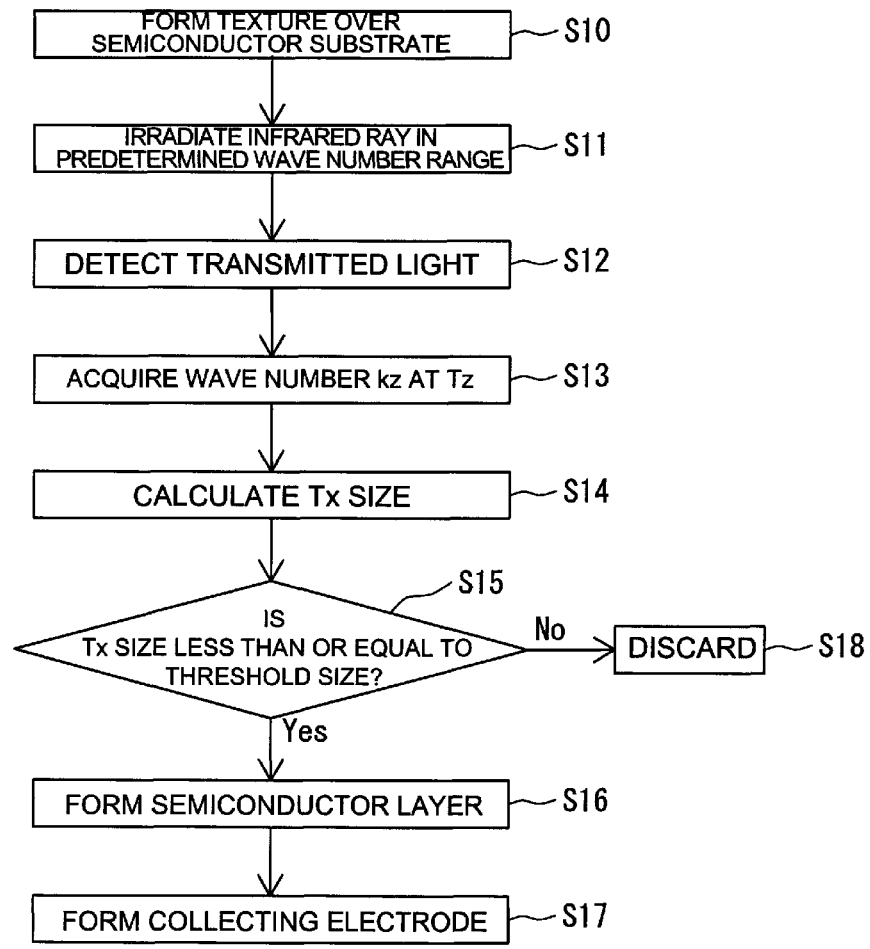
FIG. 12 is a flowchart for explaining the first example manufacturing method of the solar cell according to a preferred embodiment of the present invention.

FIGS. 11 and 12 show an example manufacturing process of the solar cell 10. A manufacturing method of the solar cell 10 will be described below, but structures and processes already described above will not be described again.

In the present manufacturing process, the Tx size is quickly measured, to manage the Tx size. The Tx size may be measured by extracting some of the substrates 21 and measuring the Tx size for those substrate 21, or may be measured for all of the substrates 21. In addition, all of the manufacturing steps including the measurement step of the Tx size may be automatically executed or a part of the steps may be manually operated. The present manufacturing process can be executed by the above-described manufacturing system 50, but the manufacturing system is not limited to the above-described system.

In the manufacturing process of the solar cell 10, first, a clean substrate 21b is prepared, and the texture 26 is formed over the light receiving surface and the back surface of the substrate 21b (S10). As described, the texture 26 is formed by immersing the substrate 21b in the etchant such as an alkali etchant. Then, the Tx size is measured (S11~S14), and the measured Tx size is compared to a threshold size (S15). The threshold size is an index for managing the Tx size, and can be arbitrarily set according to the management objective. Alternatively, a plurality of threshold sizes may be set. The threshold size is preferably an upper limit value of the Tx size. In this description, the process will be described with the threshold value being the upper limit value.

When the Tx size is determined to be less than the threshold size in S15, semiconductor layers are formed over the primary surfaces of the substrate 21 (S16). For example, the amorphous semiconductor layer 22 is formed over the light receiving surface of the substrate 21 and the amorphous semiconductor layer 24 is formed over the back surface of the substrate 21. In addition, the transparent conductive layer 23 is preferably formed over the amorphous semiconductor layer 22, and the transparent conductive layer 25 is preferably formed over the amorphous semiconductor layer 24. As described above, these thin film layers are formed by CVD or sputtering. Finally, the collecting electrode is formed over the light receiving surface and the back surface of the substrate 21 by screen printing or the like (S17), and the solar cell 10 is manufactured.

On the other hand, when it is determined in S15 that the Tx size exceeds the threshold size, the substrate 21 is discarded (S18). In this manner, for example, manufacturing of the solar cell 10 using a defective substrate 21 having the Tx size exceeding the upper limit value can be prevented. In addition, by measuring the Tx size and judging the quality before the semiconductor layer is formed, it becomes possible to not form the semiconductor layer or the like for the defective substrate 21, and for example, the manufacturing cost can be reduced.

A measurement procedure of the Tx size (S11~S14) will now be described. In the measurement of the Tx size, first, an infrared ray in a predetermined wave number range is irradiated onto a part of the primary surface of the substrate 21 over which the texture 26 is formed (S11). As described above, the wave number of the infrared ray to be irradiated can be changed according to the Tx size to be measured or the like.

Then, of the infrared ray $I_0$ irradiated onto the substrate 21, the transmitted light $I_1$ transmitted through the substrate 21 is detected (S12), and a wave number at the particular transmission detection ratio Tz (hereinafter referred to as a "wave number kz") is acquired (S13). The transmitted light $I_1$ includes the scattered component scattered by the texture 26, and a part thereof is detected, for example, by the detector 62. The transmitted light $I_1$ detected by the detector 62 is the transmitted and detected light $I_2$, and the intensity thereof differs depending on the Tx size. The wave number kz is acquired, for example, by processing the detection information by the detector 62 with a function of the computer 63.

Next, the Tx size is calculated based on the wave number kz acquired in S13 (S14). The calculation of the Tx size is executed using a predetermined function between the wave number kz and the Tx size. A specific example would be a configuration in which a relationship between the wave number kz of the infrared ray detected for the standard substrate and the Tx size of the standard substrate measured using the SEM or the like is determined in advance, and the Tx size is calculated using the relationship and the wave number kz acquired in S13. The calculation of the Tx size may be executed, for example, by a function of the calculation unit 67 of the computer 63, or may be calculated using another computing device.

Figure 13:
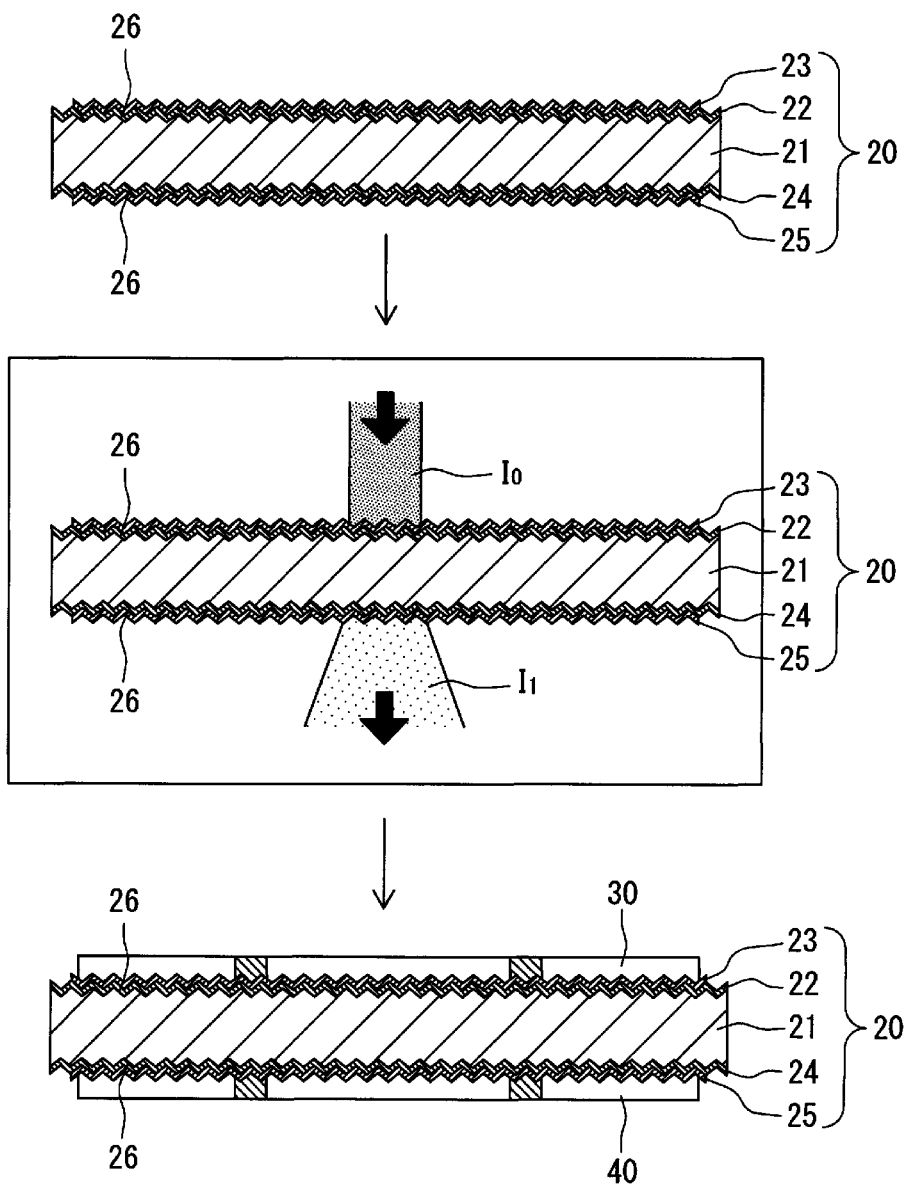
FIG. 13 is a diagram for explaining a second example manufacturing method of a solar cell according to a preferred embodiment of the present invention.
Figure 14:
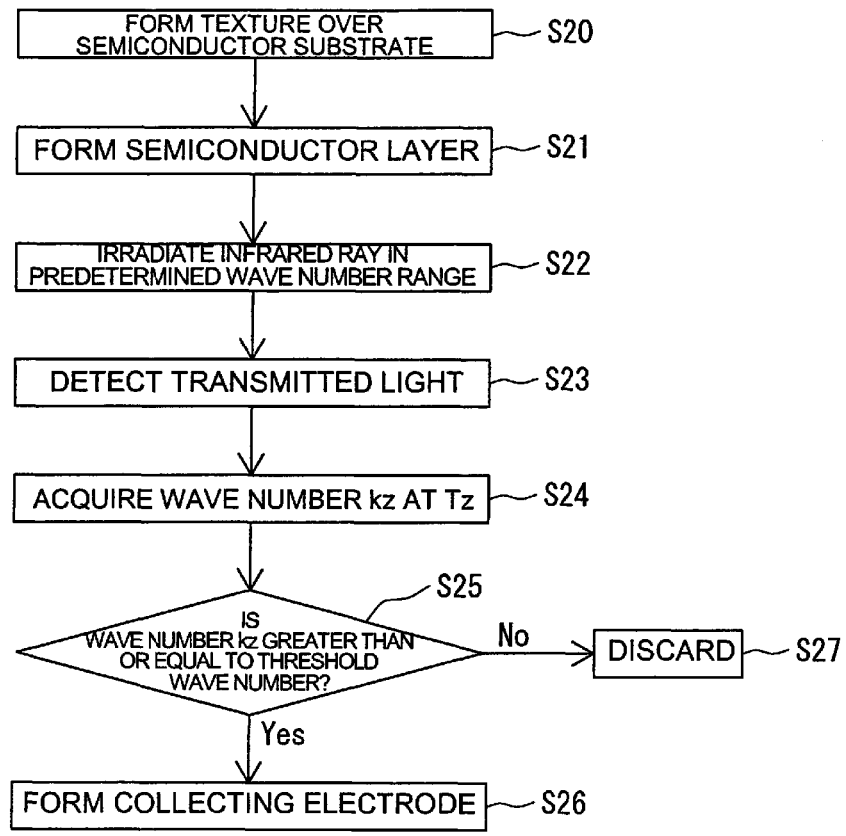
FIG. 14 is a flowchart for explaining the second example manufacturing method of the solar cell according to a preferred embodiment of the present invention.

FIGS. 13 and 14 show another example manufacturing process of the solar cell 10. Here, a difference from the process of FIGS. 11 and 12 will be primarily be described.

In the present manufacturing process, after the texture 26 is formed over the light receiving surface and the back surface of the substrate 21b (S20), the semiconductor layers (amorphous semiconductor layers 22 and 24) and the transparent conductive layers 23 and 25 are formed over the primary surfaces of the substrate 21 (S21). An infrared ray is irradiated on the substrate 21 over which the semiconductor layers or the like are formed, the transmitted light $I_1$ is detected, and the wave number kz is acquired (S22~S24). In the present manufacturing process, the wave number kz is compared with a threshold wave number without calculating the Tx size (S25). Similar to the threshold size, the threshold wave number is an index for managing the Tx size and can be arbitrarily set according to the management objective. The threshold wave number is preferably set to a value corresponding to the upper limit value of the Tx size. In other words, in the process management, the TX size does not need to be calculated, but the relationship between the wave number and the Tx size must be determined in advance.

When it is determined in S25 that the wave number kz is greater than or equal to the threshold wave number, the collecting electrodes are formed over the light receiving surface and the back surface of the substrate 21 (S26). On the other hand, when it is determined in S25 that the wave number kz is less than the threshold wave number (that is, when the Tx size exceeds the upper limit value), the substrate 21 is discarded (S27). With this process, similar to the process shown in FIGS. 12 and 13, manufacturing of the solar cell 10 using the defective substrate 21 having the Tx size exceeding the upper limit value can be prevented. In addition, by acquiring the wave number kz and judging the quality after the formation of the semiconductor layer or the like, for example, contamination at the boundary between the substrate 21 and the semiconductor layer and at the boundary between the semiconductor layer and the transparent conductive layers 23 and 25 which significantly affects the photoelectric conversion characteristic can be inhibited.

As described, according to the manufacturing process of the solar cell 10, the Tx size can be quickly measured during the process. Therefore, the Tx size can be managed in the manufacturing process without reducing the productivity of the solar cell 10. In addition, for example, with the use of the measurement device 60 exemplified in FIG. 10, a complete inspection of substrates 21 can be easily and quickly executed.

The above-described embodiment can be suitably modified in design within a range of not losing the objective of the present invention. For example, in the process shown in FIGS. 13 and 14, the Tx size may be calculated. Alternatively, the Tx size may be measured after the semiconductor layers are formed over the substrate 21 and before the transparent conductive layers 23 and 25 are formed. In this case, contamination at the boundary between the substrate 21 and the semiconductor layers can be prevented, and at the same time, ineffective processes when a defective substrate 21 is generated can be reduced.

Figure 15:
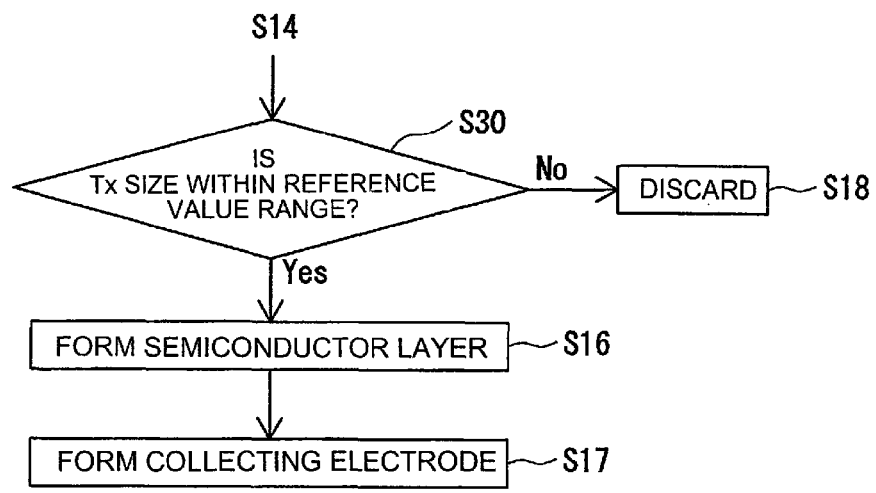
FIG. 15 is a diagram showing a first alternative configuration of a preferred embodiment of the present invention.

Alternatively, as shown in FIG. 15, as the threshold size, a lower limit value of the Tx size may be set in addition to the upper limit value of the Tx size. In FIG. 15, S10~S14 of the flowchart of FIG. 12 are not shown, and a step following S10~S14 is S30. In S30, it is judged whether or not the calculated Tx size is within a reference value range. In other words, it is judged whether or not the calculated Tx size is greater than or equal to the preset lower limit value and less than or equal to the preset upper limit value. When the Tx size is within the reference value range, it is determined that the collecting electrode is to be formed, and the semiconductor layers are formed over the primary surfaces of the substrate 21 (S16). On the other hand, when the Tx size is less than the lower limit value (that is, when the Tx size is out of the reference value range), the substrate 21 is discarded (S18). In this manner, for example, manufacturing of the solar cell 10 using a defective substrate 21 having the Tx size lower than the lower limit value can be prevented.

Similarly, S25 of the flowchart of FIG. 14 may alternatively be read as "is wave number kz within a reference value range?" In other words, it is possible to set an upper limit value of the wave number kz in addition to the lower limit value of the wave number kz as the threshold wave number, and the collecting electrodes may be formed when the wave number kz is in a reference value range which is greater than or equal to the lower limit value and less than or equal to the upper limit value.

Figure 16:
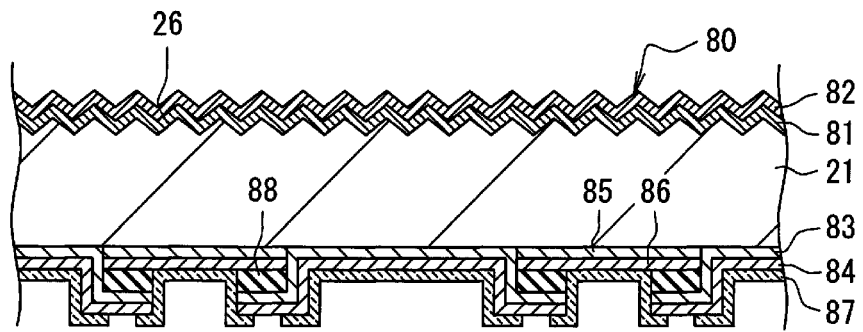
FIG. 16 is a diagram showing a second alternative configuration of a preferred embodiment of the present invention.

For the photoelectric conversion unit, a structure other than the above-described photoelectric conversion unit 20 may be employed. For example, a photoelectric conversion unit 80 shown in FIG. 16 may be employed. In the photoelectric conversion unit 80, an i-type amorphous silicon layer 81 and an n-type amorphous silicon film 82 are formed over the light receiving surface of the substrate 21, and a p-type region formed by an i-type amorphous silicon layer 83 and a p-type amorphous silicon layer 84 and an n-type region formed by an i-type amorphous silicon layer 85 and an n-type amorphous silicon layer 86 are formed respectively over the back surface of the substrate 21. In this case, the collecting electrode is provided only on the back surface side (not shown) of the substrate 21. The collecting electrode includes a p-side collecting electrode formed over the p-type region and an n-side collecting electrode formed over the n-type region. A transparent conductive layer 87 is formed between each region and each collecting electrode, and an insulating layer 88 is formed between the p-type region and the n-type region. In the form shown in FIG. 16, the texture 26 is formed only over the light receiving surface of the substrate 21.

Figure 17:
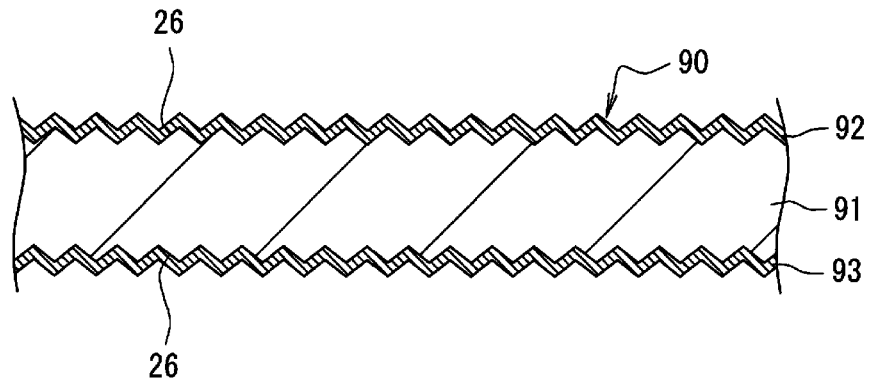
FIG. 17 is a diagram showing a third alternative configuration of a preferred embodiment of the present invention.

Alternatively, for the photoelectric conversion unit, a photoelectric conversion unit 90 shown in FIG. 17 may be employed. The photoelectric conversion unit 90 includes a p-type polycrystalline silicon substrate 91, an n-type diffusion layer 92 formed on the side of a light receiving surface of the p-type polycrystalline silicon substrate 91, and an aluminum metal film 93 formed over a back surface of the p-type polycrystalline silicon substrate 91. In the form shown in FIG. 17, the texture 26 is formed over the light receiving surface and the back surface of the p-type polycrystalline silicon substrate 91.

Figure 18:
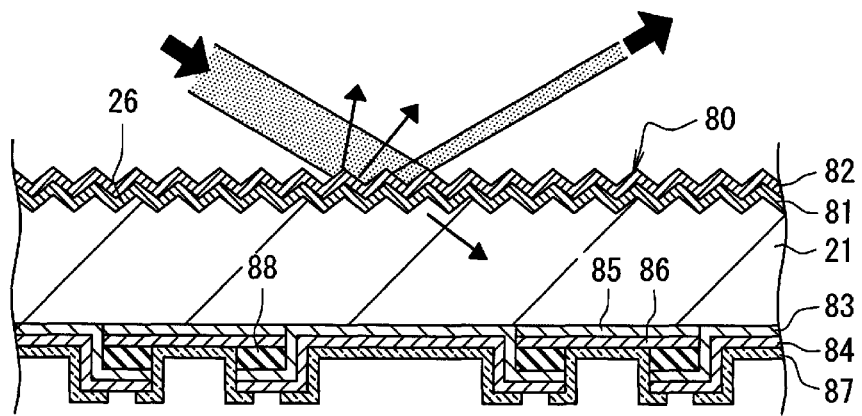
FIG. 18 is a diagram showing a fourth alternative configuration of a preferred embodiment of the present invention.

Alternatively, as shown in FIG. 18, in the manufacturing process of the solar cell, a wave number at a particular reflection detection ratio of an infrared ray reflected by the substrate 21 and detected may be acquired, and the Tx size may be managed by comparing the wave number to a threshold wave number. Alternatively, the Tx size may be calculated based on the acquired wave number using a predetermined relationship between the wave number at the particular reflection detection ratio and the Tx size. In this case, for example, a structure of a known diffusion reflection type infrared spectrophotometer may be applied to the measurement device. As described above, the extent of diffusion of the infrared ray by the texture 26 differs depending on the Tx size, and thus an intensity of reflected light at the light receiving surface over which the texture 26 is formed also differs depending on the Tx size. Therefore, by detecting the reflection light, the Tx size can be measured.

Alternatively, the Tx size of the substrate 21 in which the texture 26 is formed over both the light receiving surface and the back surface may be measured using the above-described reflected light. In this case, normally, the infrared ray is irradiated to each of the light receiving surface and the back surface, and reflected light is detected, and the Tx size on the side of the light receiving surface and the Tx size on the side of the back surface are measured, respectively.

EXPLANATION OF REFERENCE NUMERALS

10 SOLAR CELL; 20 PHOTOELECTRIC CONVERSION UNIT; 21 SUBSTRATE; 22, 24 AMORPHOUS SEMICONDUCTOR LAYER; 23, 25 TRANSPARENT CONDUCTIVE LAYER; 26 TEXTURE; 30 FIRST ELECTRODE; 31, 41 FINGER PORTION; 32, 42 BUS BAR PORTION; 40 SECOND ELECTRODE; 50 MANUFACTURING SYSTEM OF SOLAR CELL; 51 TEXTURE FORMATION UNIT; THIN FILM LAYER FORMATION UNIT; 53 ELECTRODE FORMATION UNIT; 60 MEASUREMENT DEVICE OF TEXTURE SIZE; 61 LIGHT SOURCE; 62 DETECTOR; 63 COMPUTER; 64 DIFFRACTION GRATING; 65 INTERFEROMETER; 66 AD CONVERTER; 67 CALCULATION UNIT; 68 MEMORY; 70 SAMPLE CHAMBER; 71 INCIDENT WINDOW; 72 DETECTION WINDOW; 73 HOLDER; 74 LIGHT BLOCKING PLATE; 75 SLIT; 76 OPENING.

The invention claimed is:

1. A measurement device of a texture size, comprising:
a light source that emits an infrared ray in a predetermined wave number range;
a holder that holds a substrate for a solar cell over which a texture is formed such that the infrared ray is incident over a primary surface of the substrate; and
a detector that detects an intensity of the infrared ray transmitted through the substrate.

2. The measurement device according to claim 1, wherein the holder holds the substrate such that the infrared ray is approximately vertically incident over the primary surface.

3. The measurement device according to claim 1, wherein the holder holds the substrate such that the primary surface is along a horizontal direction, and
the light source is placed above the holder in a vertical direction and the detector is placed below the holder in the vertical direction.

4. The measurement device according to claim 1, further comprising a light blocking plate that is provided between the holder and the detector and that blocks scattered light scattered by the substrate among infrared rays transmitted through the substrate.

5. The measurement device according to claim 1, wherein at least a part of the holder that contacts the substrate is made of a resin.

6. The measurement device according to claim 1, wherein the holder is of a movable type which moves in a manner such that a plurality of irradiation spots of the infrared ray on the primary surface can be set while maintaining a vertical distance from the light source and the detector to the primary surface.

7. The measurement device according to claim 1, wherein the predetermined wave number range is 50 $cm^{-1}$~10000 $cm^{-1}$.

8. The measurement device according to claim 1, further comprising:
 a memory that stores a relationship between a wave number at a particular transmission detection ratio of the infrared ray detected for a standard substrate for which the texture size is known, and the texture size thereof; and
 a calculation unit that calculates the texture size of the substrate based on the wave number at the particular transmission detection ratio of the infrared ray detected for the substrate, and the relationship.

9. A manufacturing system of a solar cell, comprising:
 the measurement device according to claim 1;
 a unit that forms the texture over the primary surface of the substrate; and
 a unit that forms a collecting electrode over the primary surface.

10. The measurement device according to claim 3, wherein the holder of the measurement device is of a movable type which can hold a plurality of substrates and which can transport the substrates in the horizontal direction.

11. A method of manufacturing a solar cell, comprising:
 after forming a texture over a primary surface of a semiconductor substrate, irradiating an infrared ray in a predetermined wave number range on a part of the primary surface over which the texture is formed, and acquiring a wave number at a particular transmission detection ratio of the infrared ray transmitted through the substrate and detected or at a particular reflection detection ratio of the infrared ray reflected by the substrate and detected; and
 forming a collecting electrode over the primary surface when the wave number is greater than or equal to a threshold wave number.

12. A method of manufacturing a solar cell, comprising:
 after forming a texture over a primary surface of a semiconductor substrate, irradiating an infrared ray in a predetermined wave number range on a part of the primary surface over which the texture is formed, and acquiring a wave number at a particular transmission detection ratio of the infrared ray transmitted through the substrate and detected or at a particular reflection detection ratio of the infrared ray reflected by the substrate and detected;
 calculating a size of the texture of the substrate based on the acquired wave number using a predetermined relationship between the wave number at the particular transmission detection ratio or at the particular reflection detection ratio, and the texture size; and
 forming a collecting electrode over the primary surface when the calculated texture size is less than or equal to a threshold size.

13. The manufacturing method according to claim 11, wherein
 the collecting electrode is formed over the primary surface when the wave number is less than or equal to the threshold wave number.

14. The manufacturing method according to claim 12, wherein
 the collecting electrode is formed over the primary surface when the calculated texture size is greater than or equal to the threshold size.

15. The manufacturing method according to claim 11, wherein
 a semiconductor layer is formed over the primary surface of the substrate for which formation of the collecting electrode is determined, and the collecting electrode is formed over the semiconductor layer.

16. The manufacturing method according to claim 11, wherein
 the infrared ray is irradiated on the part of the primary surface over which the texture is formed and the wave number is acquired after a semiconductor layer is formed over the primary surface.

17. The manufacturing method according to claim 11, wherein
 the wave number at the particular transmission detection ratio of the infrared ray is acquired after the texture is formed over both primary surfaces.

* * * * *